United States Patent [19]

Hagen et al.

[11] Patent Number: 5,210,355

[45] Date of Patent: * May 11, 1993

[54] SELECTIVE PRODUCTION OF 2,6-METHYLETHYLNAPHTHALENE

[75] Inventors: Gary P. Hagen, West Chicago; Thomas G. Smith, Naperville, both of Ill.

[73] Assignee: Amoco Corporation, Chicago, Ill.

[*] Notice: The portion of the term of this patent subsequent to Oct. 10, 2006 has been disclaimed.

[21] Appl. No.: 544,272

[22] Filed: Jun. 26, 1990

[51] Int. Cl.$^5$ ............................ C07C 5/22; C07C 5/52
[52] U.S. Cl. .................................... 585/472; 585/471; 585/474
[58] Field of Search ....................... 585/471, 472, 474

[56] References Cited

U.S. PATENT DOCUMENTS

| | | | |
|---|---|---|---|
| 2,388,758 | 11/1945 | Mills, Jr. .............................. | 585/474 |
| 4,454,364 | 6/1984 | Farcasiu et al. ..................... | 585/472 |
| 4,873,386 | 10/1989 | Hagen et al. ........................ | 585/472 |
| 4,950,824 | 8/1990 | Shiroto et al. ...................... | 585/474 |

FOREIGN PATENT DOCUMENTS 0116353 10/1978 Japan .

*Primary Examiner*—Patrick P. Garvin
*Assistant Examiner*—E. D. Irzinski
*Attorney, Agent, or Firm*—Thomas E. Nemo; Wallace L. Oliver; Frank J. Sroka

[57] ABSTRACT

A method for the highly selective production of 2,6-methylethylnaphthalene involving the use of a specific acid catalyst and a highly regeospecific ethylating agent.

15 Claims, No Drawings

SELECTIVE PRODUCTION OF 2,6-METHYLETHYLNAPHTHALENE

BACKGROUND OF THE INVENTION

1. Field of the Invention

This invention relates to the production of a specific dialkylnaphthalene and more particularly concerns the highly selective production of 2,6-methylethylnaphthalene by the transethylation of 2-methylnaphthalene.

2. Description of the Prior Art 2,6-Naphthalene dicarboxylic acid is a monomer that is known to be useful for the preparation of a variety of polymers. For example, poly(ethylene 2,6-naphthalate) which has better heat resistance and mechanical properties than polyethylene terephthalate and is useful in the manufacture of films and fibers is prepared from 2,6-naphthalene dicarboxylic acid and ethylene glycol.

2,6-Dialkylnaphthalenes are desirable feedstocks for oxidation to 2,6-naphthalene dicarboxylic acid. A known conventional process for producing 2,6-naphthalene dicarboxylic acid comprises the oxidation of a 2,6-dialkylnaphthalene with oxygen in the liquid phase in an acetic acid solvent at an elevated temperature and pressure and in the presence of a catalyst comprising cobalt, manganese and bromine components.

Dialkylnaphthalenes can be found in low concentrations in refinery streams as mixtures of some or all of the many possible dialkylnaphthalene isomers. However, separation of these isomers is very difficult and expensive. Consequently, methods for producing specific dialkylnaphthalenes or mixtures of two or three specific dimethylnaphthalenes in high purity and quality are highly desirable. Olah et al., "Alkylation of Naphthalene with Alkyl Halides," Journal of American Chemical Society, 98:7, pages 1839-1842 (Mar. 31, 1976) disclose that theretofor there was no clear understanding of directive effects and selectivities for the Friedel-Crafts alkylation of naphthalene.

Since then, Japanese Kokai Patent Application Publication No. 61-83137 Apr. 26, 1986) discloses a synthesis involving the transalkylation of naphthalene or 2-methylnaphthalene in the presence of an aluminum chloride catalyst at 0°-35° C. in the liquid phase to produce a 2,6-dialkylnaphthalene. Suitable alkylating agents are disclosed as including durene, diethylbenzene, triethylbenzene, triisopropylbenzene, isopropylxylene, and dibutylbenzene. The reported results indicate a relatively low degree of selectivity for the formation of specific dialkylnaphthalenes. Furthermore, it is specifically stated that the disclosed alkylation method must be performed at 0°-35° C., preferably room temperature, and that the higher the reaction temperature, the lower the selectivity for the formation of beta-alkyl substituted naphthalene and especially 2,6-dialkylnaphthalene. In addition, although this published patent application specifically mentions durene (1,2,4,5-tetramethylbenzene) as an example of an alkylation agent, it contains actual examples that illustrate only the use as alkylating agents in the method disclosed therein of polyalkylbenzenes where the alkyl groups are larger than methyl groups, and indicates as follows that polyalkylbenzenes with alkyl groups other than methyl groups afford benefits in the method disclosed therein: "Polyalkylbenzenes with ethyl, propyl, or butyl groups with high-carbon alkyl groups have high reaction rates . . . " Moreover, this published Japanese patent application states that, when the naphthalene is solid at the reaction temperature, a solvent such as a paraffin or cycloparaffin should be employed. This published Japanese patent application also discusses the use of halogenated alkyls in the alkylation of naphthalenes as a prior art method which did not produce a betaalkyl naphthalene with the desired selectivity.

Japanese Kokai Patent Application Publication No. 62-252733 (Nov. 4, 1987) discloses a process for the transethylation of biphenyl with an ethylbenzene to form monoethylbiphenyl and diethylbiphenyl in the presence of a Friedel-Crafts catalyst, such as aluminum chloride, at 70°-150° C. This published Japanese patent application discloses that a reaction temperature of less than 70° C. delays the reaction rate. The ring positions of the ethyl substituents in the ethylated biphenyl products are not disclosed. Suitable ethylbenzenes are disclosed as including ethylbenzene, diethylbenzene, triethylbenzene, tetraethylbenzene, other ethyl-substituted benzenes, ethyltoluene, diethyltoluene and other ethyl-substituted toluenes. Polyethylbenzenes containing relatively small amounts of monoethylbenzene, triethylbenzene and tetraethylbenzene can also be used advantageously.

Shimada et al., "Ethylation and Transethylation of Naphthalene," Bulletin of the Chemical Society of Japan, Vol. 48 (II), pages 3306-3308 (November, 1975), disclose the transethylation of naphthalene by ethylbenzene or ethylxylenes to form monoethylnaphthalenes in the presence of an aluminum chloride catalyst at 20°-30° C. The rates of transethylation with ethylxylene isomers were reported to decrease in the order of 1,2-dimethyl-4-ethylbenzene≧, 1,3-dimethyl-4-ethylbenzene≧, 1,4-dimethyl-2-ethylbenzene ≧1,3-dimethyl-5-ethylbenzene.

Japanese Patent Application 26/336, published on Oct. 18, 1989, discloses a method for the preparation of ethyldiphenylethane or diethyldiphenylethane by the transethylation of diphenylethane with polyethylbenzene(s) in the presence of a Friedel Crafts catalyst at 0°-150° C. Preferred catalysts are aluminum chloride, aluminum bromide and boron trifluoride. Transethylation of 1,1-diphenylethane by this method produces either 1-phenyl-1-ethylphenylethane, 1-phenyl-1-diethylphenylethane or 1,1-bis(ethylphenyl)ethane. The ring positions of the ethyl substituents in the ethylated products are not disclosed.

Thus, until recently, no existing method was known for the highly selective production of 2,6-dialkylnaphthalene or of a mixture of 2,6- and 2,7-dialkylnaphthalenes by a transalkylation process. Then Hagen et al., U.S. Pat. No. 4,873,386, which issued on Oct. 10, 1989, disclosed a method for producing 2,6-diethylnaphthalene, which comprises: reacting in the liquid phase at least one of naphthalene or 2-ethylnaphthalene as the feed with at least one of 1,4-diethylbenzene, 1,2,4-triethylbenzene, at least one tetraethylbenzene or pentaethylbenzene as the ethylating agent per mole of the feed by weight, in the presence of a Lewis acid catalyst selected from the group consisting of aluminum chloride, aluminum bromide, tantalum pentachloride, antimony pentafluoride, and red oil, at a level of from about 0.01 to about 1 mole of the catalyst per mole of the feed (for red oil, based on the aluminum chloride content of the red oil) by weight and at a temperature in the range of from about −10° C. to about 100° C. In particular, Hagen et al., disclose that 1,2,3,4- and 1,2,3,5-tetraethylbenzenes, as well as 1,2,4,5-tetraethylbenzene, are useful ethylating agents, but that hexaethylbenzene is not. Hagen et al. further disclose that 2,6-diethylnaphthalene is formed at a higher selectivity and yield when 2-ethylnaphthalene is transethylated and that pentaethylbenzene and any tetraethylbenzene are the preferred ethylating agents.

Furthermore, it has been discovered that the oxidation of 2,6-dialkylnaphthalene proceeds with substantially less by-product formation when the alkyl groups are ethyl groups than when the alkyl groups are methyl groups, and thus that the crude 2,6-naphthalene dicarboxylic acid formed by the oxidation of 2,6-diethylnaphthalene can be purified to polymer grade purity more readily than can crude 2,6-naphthalene dicarboxylic acid formed by the oxidation of 2,6-dimethylnaphthalene. For this reason, the aforesaid transethylation method of Hagen et al. is especially desirable.

However, because of the relative unavailability of 2-ethylnaphthalene compared to the greater availability of 2-methylnaphthalene for use as the preferred feedstock for the aforesaid method of Hagen et al., and because of the benefit in efficiency in oxidizing the 2,6-dialkylnaphthalene of the lowest possible molecular weight to 2,6-naphthalene dicarboxylic acid, it is highly desirable to devise a method for the Friedel-Crafts transethylation of 2-methylnaphthalene to 2,6-methylethylnaphthalene. 2,6-methylethylnaphthalene is a compromise oxidation feedstock which would afford the benefits of a 2,6-dialkylnaphthalene both having the next to the lowest molecular weight of any dialkylnaphthalene and having one ethyl substituent for oxidation with substantially less by-product formation. Thus, it is highly desirable to provide a method for producing 2,6-methylethylnaphthalene by transethylation of a more relatively available feedstock than 2-ethylnaphthalene.

OBJECTS OF THE INVENTION

It is therefore a general object of the present invention to provide an improved method for the highly selective production of 2,6-methylethylnaphthalene or a mixture of 2,6- and 2,7-methylethylnaphthalenes.

More specifically, it is an object of the present invention to provide an improved method for the highly selective production of 2,6-methylethylnaphthalene or a mixture of 2,6- and 2,7-methylethylnaphthalenes by transethylating 2-methylnaphthalene under highly regiospecific conditions.

Other objects and advantages of the invention will become apparent upon reading the following detailed description and appended claims.

SUMMARY OF THE INVENTION

These objects are achieved by an improved method for producing 2,6-methylethylnaphthalene, comprising: reacting 2-methylnaphthalene as the feed in the liquid phase with an ethylating agent selected from the group consisting of at least one of 1,2,4-triethylbenzene, any tetraethylbenzene, or pentaethylbenzene at a level of from about 1 to about 10 moles of the ethylating agent per mole of the feed, in the presence of a Lewis acid or a Bronsted acid alkylation catalyst or a mixture thereof that is more acidic than ferric chloride and at least as acidic as ferric bromide, at a level of from about 0.01 to about 1 mole of the catalyst per mole of the feed and at a temperature in the range of from about $-10°$ C. to about $100°$ C.

DETAILED DESCRIPTION OF THE PREFERRED EMBODIMENTS 2-methylnaphthalene is the feed in the method of this invention. The feed must be either dissolved in a suitable solvent as described hereinbelow or must be a liquid at the reaction temperature employed.

Relative to the diethylbenzenes and 1,2,3- and 1,3,5-triethylbenzenes, polyethylated benzenes having from 3 up to 5 ethyl substituents on the benzene ring, two of which are para to one another, afford substantially improved yields of the desired 2,6-methylethylnaphthalene in the method of this invention. Thus, 1,2,4-triethylbenzene, any tetraethylbenzene, pentaethylbenzene, and mixtures thereof are the only suitable ethylating agents in the method of this invention. Since all tetraethylbenzenes have at least one pair of ethyl substituents that are in ring positions that are located para to each other, all tetraethylbenzenes are suitable ethylating agents in the method of this invention, and therefore, mixtures of tetraethylbenzene isomers need not be separated and can be used as such as the ethylating agent in the method of this invention. Hexaethylbenzene forms an irreversible addition complex with the acid catalyst, and therefore, is not an effective ethylating agent in the method of this invention. Preferably, a tetraethylenebenzene, and more preferably 1,2,4,5-tetraethylbenzene, is the ethylating agent in the method of this invention. The mole ratio of the ethylating agent to 2-methylnaphthalene is in the range of from about 1:1, preferably from about 2:1, to about 10:1, preferable to about 5:1, in the method of this invention.

The transethylation reaction of the present invention is conducted in the liquid phase in the presence or absence of a solvent. Any liquid that is inert under the reaction conditions employed and serves as an effective solvent for the reactants and products is suitable for use in the method of this invention. Suitable solvents include halocarbons, such as methylene chloride, chlorobenzene, 1,1-dichloroethane, 1,2-dichloroethane, and chloroform, or carbon disulfide, benzene, cyclohexane, and n-octane. Solvents which are basic and bind irreversibly with the catalyst are not suitable. Such unsuitable solvents include ketones, aldehydes, ethers, esters and alcohols. Preferably, the solvent is methylene chloride. If a solvent is employed, the weight ratio of solvent-to-feed compound is in the range of from about 1:1, preferably from about 2:1, to about 15:1, preferably to about 8:1.

Lewis acids and Bronsted acids or mixtures thereof that are conventionally used as alkylation catalysts and that are more acidic than ferric chloride and at least as acidic as ferric bromide and preferably at least as acidic as aluminum chloride and that do not decompose under the conditions employed in the method of this invention, are suitable for use as the catalyst in the method of this invention. Suitable Lewis acid catalysts include aluminum chloride, aluminum bromide, tantalum pentachloride, antimony pentafluoride, boron trichloride, ferric bromide, sulfonated zirconia, trifluoromethanesulfonic acid, and "red oil," a complex polar liquid catalyst phase which is synthesized by addition of ethyl chloride or bromide or hydrogen chloride or bromide to a slurry of aluminum chloride or some other aforesaid suitable Lewis Acid in an aromatic solvent such as benzene, methylbenzene, ethylbenzene, mixed dimethylbenzenes, mixed diethylbenzenes, mixed tetramethylbenzenes or mixed tetraethylbenzenes and which forms a separate liquid phase below the phase containing the feed. Preferably, aluminum chloride or red oil containing aluminum chloride is the catalyst. Other conventional Lewis acids, such as antimony chloride, bismuth chloride, ferric chloride, tin chloride, titanium chloride, and zinc chloride are not such effective catalysts in the method of the present invention.

The catalyst can be employed as a separate immiscible layer such as the aforementioned red oil, or it can be dissolved with the reactants and products in an organic solvent such as methylene chloride or chlorobenzene. Thus, depending upon the selection of solvent for the catalyst, the feed, ethylating agent and catalyst can be present in a single liquid phase, or the feed and catalyst can be present in separate liquid phases. In the alternative, the catalyst can be in the form of a solid, for example, aluminum chloride deposited or intercalated with graphite. The catalyst is employed in the method of this invention at a level in the range of from about 0.01, preferably from about 0.05, to about 1.0, preferably to about 0.2 mole per mole of 2-methylnaphthalene.

If the reaction is performed continuously or batchwise, the residence time is from 0.1, preferably from about 1, to about 10, preferably to about 5 hours. The reaction temperature is in the range of from about −10° C., preferably from about −5° C., to about 100° C., preferably to about 20° C. The reaction pressure must be sufficiently high to maintain the reactants and products in the liquid phase at the particular reaction temperature employed and generally is in the range of from about 0.5, preferably from about 0.8, to about 10, preferably to about 5, atmospheres gauge.

Preferably, when a polar solvent is not used, a hydrogen halide, such as hydrogen chloride, or an alkyl, alkylene or alkylidene halide is employed as a promoter in the method of the present invention. Typically, such alkyl, alkylene, or alkylidene halides include a methyl halide, such as methyl chloride, or a methylene, ethylene, or ethylidine halide. The promoter is employed at a level of from about 0.1, preferably from about 0.5, up to about 100, preferably up to at least about 2 moles per mole of catalyst (for red oil, based on the aluminum chloride content of the red oil). When the solvent is an alkyl or alkylene halide, it also serves as a promoter in the method of the invention.

The present invention will be more clearly understood from the following specific examples:

EXAMPLES 1-3

Except as indicated hereinbelow, each of Examples 1-3 was performed using a 250 milliliter, 3-neck, round-bottom flask equipped with a magnetic stirrer, purged with nitrogen and cooled in an ice bath. The components of the reaction mixture that are identified in Table 1 were introduced in the amounts and under the reaction conditions specified in Table 1. In each case, the catalyst was introduced last, at which point the transethylation reaction commenced immediately: Twenty-four hours after the catalyst was introduced, methanol, in a volume that was approximately twice the volume of the reaction medium, was introduced to quench the reaction. The product mixture was then analyzed to determine the weight percent of benzene, toluene, or 2-methylnaphthalene (identified as 2-MN, in Table 2) that is converted ("Conversion of 2-MN"), the "Yield" or mole percent of 2-methylnaphthalene that is converted selectively to each of 2,6-methylethylnaphthalene (identified as 2,6-MEN) and 2,7-methylethylnaphthalene (identified as 2,7-MEN), and the "Selectivity" or relative mole percent of 2,6-methylethylnaphthalene and 2,7-methethylnaphthalene in the combined amounts of products produced in each example. The Yield is also the quotient obtained by dividing 100 into the product of the Conversion multiplied by the Selectivity. In Table 1, TeEB means a mixture of tetraethylbenzene isomers.

TABLE 1

| Example No. | Feed | Ethylating Agent Compound | Amount[1] | Catalyst Compound | Amount[1] | Reaction Temperature (°C.) | Solvent | Promoter Compound | Amount[2] |
|---|---|---|---|---|---|---|---|---|---|
| 1 | 2-MN | TeEB | 2 | AlCl$_3$ | 0.26 | 40 | None | EtBr | 0.26/11.357 |
| 2 | 2-MN | TeEB | 2 | AlCl$_3$ | 0.25 | 90–60 | None | EtBr | 0.25/11.868 |
| 3 | 2-MN | TeEB | 2 | AlCl$_3$ | 0.26 | 50–35 | None | EtBr | 0.26/11.354 |

Footnotes
[1] moles per mole of 2-MN
[2] moles per actual number of moles of 2-MN used

TABLE 2

| Example No. | Reaction Time (min) | Conversion of Feed | Yield 2,6-MEN | 2-7-MEN | Selectivity 2,6-MEN | 2-7-MEN |
|---|---|---|---|---|---|---|
| 1 | 15 | 17.2 | 14.0 | 3.6 | 81.4 | 15.1 |
|   | 34 | 36.4 | 30.5 | 5.9 | 83.8 | 16.2 |
|   | 49 | 53.0 | 43.7 | 9.2 | 82.5 | 17.4 |
|   | 64 | 66.4 | 53.7 | 11.9 | 80.9 | 17.9 |
|   | 84 | 78.0 | 62.7 | 14.5 | 80.4 | 18.6 |
|   | 98 | 82.2 | 60.5 | 14.4 | 73.6 | 17.5 |
| 2 | 15 | 74.3 | 57.6 | 15.8 | 77.5 | 21.3 |
|   | 30 | 81.5 | 59.8 | 17.1 | 73.4 | 21.0 |
| 3 | 15 | 4.5 | 3.5 | 0.5 | 77.8 | 11.1 |
|   | 35 | 9.9 | 8.6 | 1.2 | 86.9 | 12.1 |
|   | 80 | 30.0 | 25.5 | 4.5 | 85.0 | 15.0 |
|   | 105 | 45.2 | 38.3 | 6.9 | 84.7 | 15.3 |
|   | 125 | 57.8 | 48.3 | 9.4 | 83.6 | 16.3 |
|   | 145 | 65.7 | 54.3 | 10.3 | 82.6 | 15.7 |
|   | 155 | 68.7 | 54.7 | 10.8 | 79.6 | 15.7 |
|   | 185 | 76.1 | 58.6 | 11.9 | 77.0 | 15.6 |
|   | 215 | 83.6 | 61.1 | 12.9 | 73.1 | 15.4 |

The results in Table 2 illustrate that, regardless of the differences in the resulting reaction rates, the use of different reaction temperatures affords similarly high yields of 2,6-methylethylnaphthalene provided that the reaction is permitted to proceed for sufficiently long times. In addition, the use of relatively lower reaction temperatures affords the highest and most favorable ratios of the amount of 2,6-methylethylnaphthalene produced-to-the amount of 2,7-methylethylnaphthalene produced.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A method for producing 2,6-methylethylnaphthalene comprising: reacting 2-methylnaphthalene as the feed in the liquid phase with at least one of 1,2,4-triethylbenzene, at least one tetraethylbenzene or pentaethylbenzene as the ethylating agent, at a level of from about 1 to about 10 moles of the ethylating agent per mole of the feed, in the presence of a catalyst comprising a Lewis acid or Bronsted acid alkylation catalyst or mixture thereof that is more acidic than ferric chloride and at least as acidic as ferric bromide, at a level of from about 0.01 to about 1 mole of the catalyst per mole of the feed and at a temperature in the range of from about −10° C. to about 100° C.

2. The method of claim 1 wherein the ethylating agent comprises a tetraethylbenzene, pentaethylbenzene, or a mixture thereof.

3. The method of claim 2 wherein the ethylating agent comprises a tetraethylbenzene.

4. The method of claim 1 wherein the ethylating agent is at a level of from about 2 to about 5 moles per mole of the feed by weight.

5. The method of claim 1 wherein the catalyst comprises aluminum chloride, aluminum bromide boron trichloride, tantalum pentachloride, antimony pentafluoride, ferric bromide, sulfonated zirconia, trifluoromethanesulfonic acid or red oil.

6. The method of claim 1 wherein the catalyst comprises red oil or aluminum chloride.

7. The method of claim 1 wherein the catalyst is at a level of from 0.05 to about 0.2 mole per mole of the feed.

8. The method of claim 1 wherein the reaction is conducted at a temperature in the range of from about −5° C. to about 20° C.

9. The method of claim 1 wherein the reaction is conducted in the presence of a promoter comprising a hydrogen halide or an alkyl, alkylene or alkylidene halide, at a level of from about 0.1 to about 100 moles per mole of the catalyst.

10. The method of claim 9 wherein the promoter is hydrogen chloride or methylene chloride.

11. The method of claim 1 wherein the feed and ethylating agent are dissolved in a solvent.

12. The method of claim 1 wherein the catalyst is dissolved in a solvent.

13. The method of claim 1 wherein the feed, ethylating agent and catalyst are present in a single liquid phase.

14. The method of claim 1 wherein the feed and catalyst are present in separate liquid phases.

15. The method of claim 1 wherein the catalyst is in the solid phase.

* * * * *

UNITED STATES PATENT AND TRADEMARK OFFICE
CERTIFICATE OF CORRECTION

PATENT NO. : 5,210,355
DATED : May 11, 1993
INVENTOR(S) : Gary P. Hagen, et. al.

It is certified that error appears in the above-indentified patent and that said Letters Patent is hereby corrected as shown below:

Column 2, line 36, "26/336" should read --261336--.

Signed and Sealed this

Thirtieth Day of August, 1994

Attest:

BRUCE LEHMAN

*Attesting Officer*     *Commissioner of Patents and Trademarks*